United States Patent [19]
Mintz

[11] Patent Number: 4,797,369
[45] Date of Patent: Jan. 10, 1989

[54] METHOD AND APPARATUS FOR DETECTING A BLOOD CLOT

[75] Inventor: Michael Mintz, Edison, N.J.

[73] Assignee: International Technidyne Corp., Edison, N.J.

[21] Appl. No.: 720,575

[22] Filed: Apr. 5, 1985

[51] Int. Cl.[4] ............................................. G01N 33/86
[52] U.S. Cl. ........................................ 436/69; 422/73; 436/150
[58] Field of Search ................. 356/39; 324/446, 71.1; 422/73; 436/69, 150, 151

[56] References Cited

U.S. PATENT DOCUMENTS

| | | |
|---|---|---|
| 3,268,804 | 8/1966 | Young ................... 422/73 |
| 3,566,163 | 2/1971 | Mittleman ............... 422/73 |
| 3,605,010 | 9/1971 | Folus ................... 422/73 |
| 3,704,099 | 11/1972 | Sanz ................... 422/73 |
| 3,814,585 | 6/1974 | Bailly ................... 422/73 |
| 4,184,486 | 1/1980 | Papa ................... 128/734 |
| 4,240,438 | 12/1980 | Updike et al. .......... 128/635 |
| 4,267,081 | 5/1981 | Seneker ................. 525/7 |
| 4,276,260 | 6/1981 | Drbal et al. ............ 422/63 |
| 4,326,851 | 4/1982 | Bello et al. ............ 422/64 |

FOREIGN PATENT DOCUMENTS 1022822  1/1958  Fed. Rep. of Germany ........ 356/39

*Primary Examiner*—Michael S. Marcus
*Attorney, Agent, or Firm*—Arthur L. Plevy

[57] ABSTRACT

A sample of whole blood or blood plasma is dispensed into two or more zones. The zones are separated and brought together repeatedly such that the blood sample is divided into multiple parts each associated with a zone. The parts are then rejoined into a single part and the process of separation continues. During the process, a liquid bridge between the separating parts is initially supported by surface tension but eventually collapses at the point of maximum zonal separation. When a fibrin clot is entrained within the rejoined part, it will align in a direction parallel to the direction of the relative motion between the zone. In this manner a thread appears between the parts as they are being separated. This thread is indicative of a clot which clot is capable of being detected by visual or electrical conductivity means. The apparatus depicted performs the above noted operations and automatically provides an output signal upon detection of the fibrin clot.

10 Claims, 3 Drawing Sheets

PHASE 5

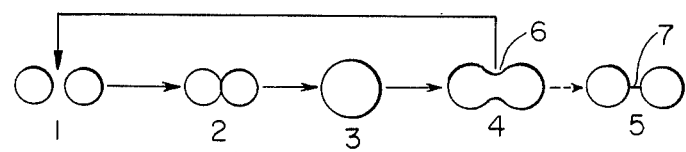
F I G. 1
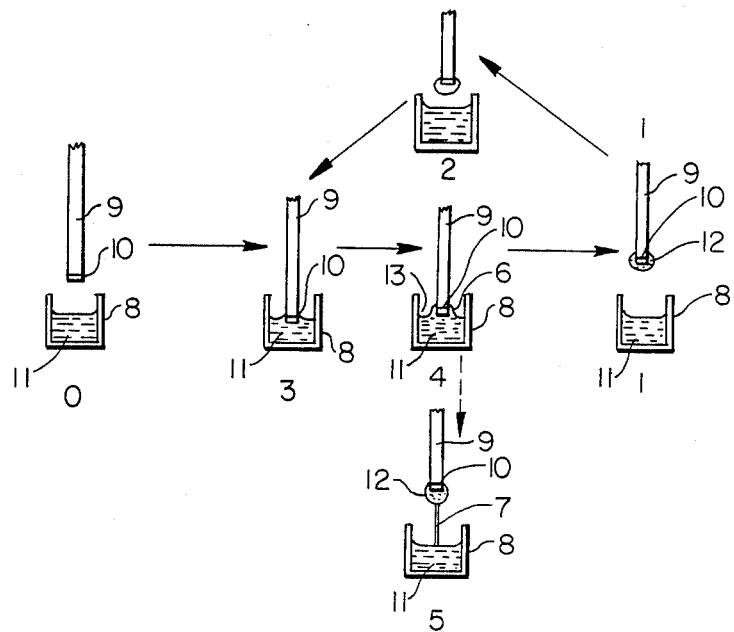
F I G. 2
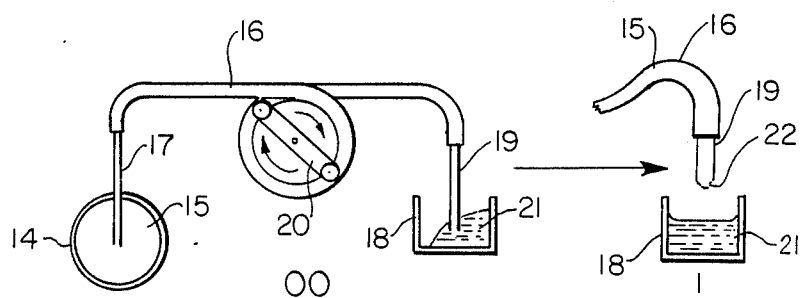
F I G. 3

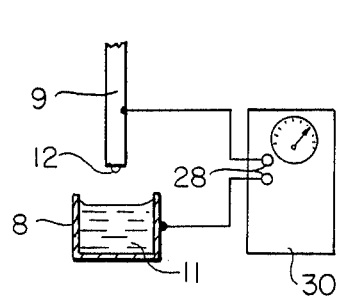
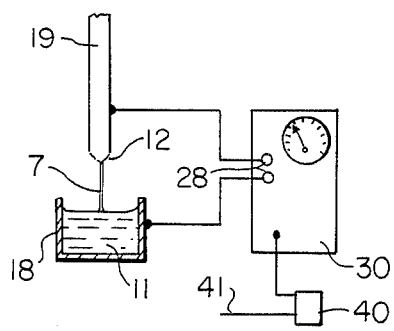
F I G. 4A    F I G. 4B
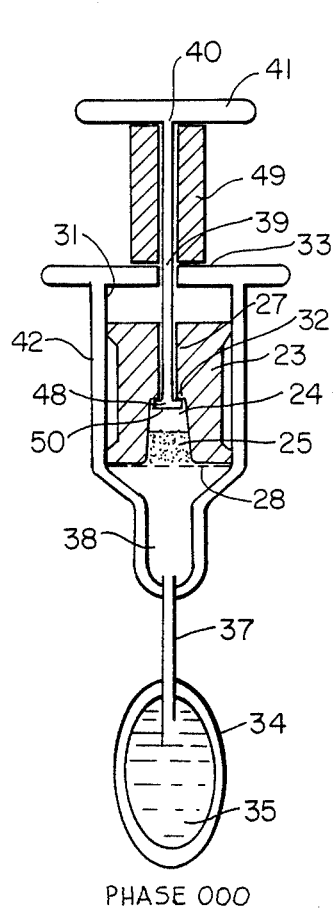
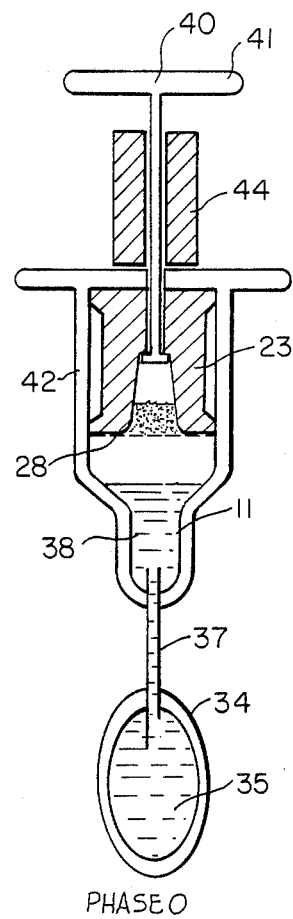
F I G. 5A    F I G. 5B

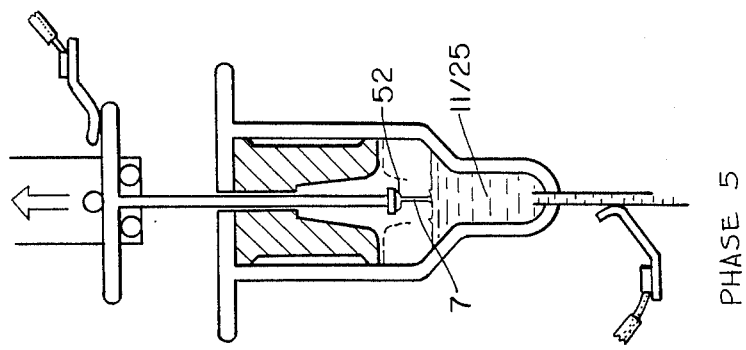
FIG. 5F PHASE 5
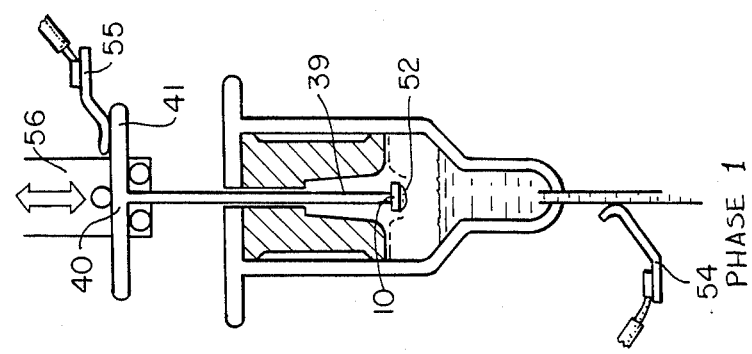
FIG. 5E PHASE 1
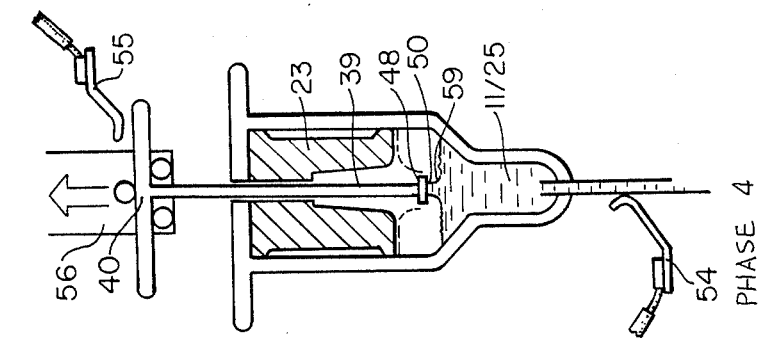
FIG. 5D PHASE 4
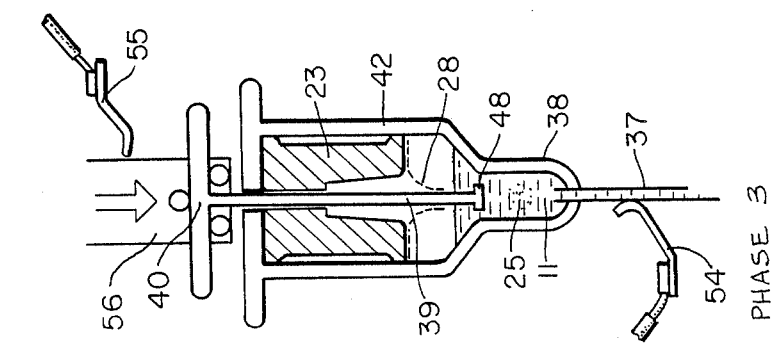
FIG. 5C PHASE 3

METHOD AND APPARATUS FOR DETECTING A BLOOD CLOT

THE BACKGROUND OF THE INVENTION

This invention relates to the detection of a blood clot and more particularly to the in vitro detection of a fibrin clot in a whole blood or blood plasma sample.

In vitro blood coagulation tests are performed clinically for purposes of analyzing the status of a patient's hemostatic or blood coagulation processes as such processes may relate to therapies or natural condition. The practice of in vitro blood coagulation analysis may be broken down into two categories. The first of these relates to indirect methods, usually involving some form of assay in which the analyte is an enzyme, clotting factor or medication and the effect upon ultimate in vivo thrombus formation is implied from the in vitro determination analyte concentration. The second category relies on clot time, that is an in vitro analysis of the time required for a blood sample or blood sample/reagent mixture to be transformed from its liquid state to one in which polymerized solid material is detected. Inferred from data resulting from clot timing analysis is the tendency for the in vivo formation of polymerized solid material.

Clot timing methods are further broken down into two approaches, photo-optical (turbidometric) and mechanical. Turbidometric clot sensors are generally limited to analyses of essentially transparent blood plasma samples. Mechanical methods, on the other hand, typically identify solidified material in a whole blood or plasma sample by making direct physical contact with the solidified material. In one such mechanical detection system, forces are directed from one mechanical element through the fibrin mass, to another mechanical element, a magnet. The resulting change in position of the latter is interpreted electronically by a magnetic field sensitive component to be indicative of the presence of a clot (see U.S. Pat. No. 3,695,842-METHOD AND SYSTEM FOR ANALYZING A LIQUID by M. Mintz issued on Oct. 3, 1972.) In another mechanical clot detection system, a needle is passed through a drop of blood and is examined for the presence of fibrin strands as it is withdrawn from the liquid surface (see Osgood, Edwin D. A TEXTBOOK OF LABORATORY DIAGNOSIS, 3rd. Ed., The Blakiston Company,. Philadelphia, 1940, p. 503). An automated embodiment of the "drop and needle method" is described in U.S. Pat. Nos. 3,267,362; 3,267,363; 3,267,364 and 3,268,804 wherein a fibrin strand is withdrawn from a liquid blood sample and thereafter comprises an electrically conductive path for signaling the occurrence of the clot-forming process. In an additional mechanical clot-detection scheme, a blood sample is drawn into a glass capillary tube from which small lengths are broken from one end at prescribed time intervals. The visual observation of a fibrous strand joining the broken and primary pieces of tubing is interpreted as an end point for clot detection (see Frankel and Reitman, Ed. GRADWOHL'S CLINICAL LABORATORY METHODS AND DIAGNOSIS 6 Ed. The C. V. Mosby Company, Saint Louis, 1963, p. 1199).

Some perceived disadvantage of the described prior art systems include moderate sensitivity, large blood sample volume requirements, inconvenience with regard to repetitive testing systems and occasionally unreliable test results.

Accordingly, it is the object of the present invention to provide an improved method and apparatus for reliably detecting the presence of a fibrous blood clot.

It is an additional object of the present invention to minimize blood sample volume requirements such that a multiplicity of coagulation timing tests on a single patient that utilize the invention may be performed without undue hazard to the patient.

It is an additional object of the present invention to provide a means whereby blood samples may be automatically collected from a vessel, transferred to a test zone and clot detection implemented.

It is still a further object of the present invention to provide a system whereby blood samples may be drawn into a collecting syringe and the test to identify fibrin clot formation performed within the body of the syringe itself.

BRIEF DESCRIPTION OF THE PREFERRED EMBODIMENT

A system and method of detecting a fibrous blood clot in a liquid blood sample. A sample of whole blood or blood plasma is dispensed into two or more zones. The zones are separated and brought together repeatedly, such that the blood sample is divided into multiple parts each associated with a zone and rejoined into a single part. A liquid bridge between the separating parts is initially supported by surface tension but eventually collapses at the point of maximum zonal separation. When a fiberous clot is entrained within the rejoined part, it tends to align itself in a direction parallel to the direction of relative motion between the zones, and in this manner is drawn into the bridge between separating parts. In the presence of such a clot liquid blood gently wicks out of the bridge along the fibrin clot and into the individual zones at their point of maximum separation. The fibrin clot remains joining the zones to be identified by visual or electrical conductivity means.

BRIEF DESCRIPTION OF THE FIGURES

FIG. 1 is a diagrammatic view illustrating the phases to which a blood sample is subjected for the detection of a fibrin clot.

FIG. 2 is a example of apparatus used for detecting the formation of a fibrin clot.

FIG. 3 is an example of alternate apparatus according to this invention.

FIG. 4A depicts an electrical system for responding to the detection of a fibrin clot according to this invention.

FIG. 4B depicts an electrical system including a timer for fibrin clot detection.

FIGS. 5A to 5F illustrate apparatus and the various phases of the operation of the apparatus for detecting the formation of a clot in whole blood or plasma.

DETAILED DESCRIPTION OF THE FIGURES

Referring to FIG. 1, there is shown a diagrammatic illustration of the phases of a blood sample in a basic system for detecting the formation of a fibrin clot. Numeral 1 represents a blood sample which essentially consists of two parts indicative of a first and a second zone. Numeral 2 indicates that the two parts of the blood sample are being moved closer together. As the parts are moved closer together and come into contact, they form a single droplet of blood as indicated by numeral 3. The two parts of the blood sample have been brought into contact with one another and the surface tension between the two parts has been overcome thus forming the single droplet as depicted by numeral 3. The single droplet 3 is then divided or pulled apart as indicated by reference numeral 4.

A bridge 6 between the blood parts is supported by surface tension until the parts have been moved far enough apart to overcome the bridge surface tension. This, for example, may be 60 thousandths of an inch for a 20 microliter blood sample. Thus as can be seen, at the stage or phase indicated by reference numeral 4, the single blood droplet is pulled apart and if it is successfully pulled apart then one continues the process and goes through the steps shown and indicated by numerals 1 to 4.

In this instance which is in the absence of a fibrin clot between the blood clots the sample is thereby restored to the condition shown in phase 1. If a fibrin clot is entrained in the bridge 6, the gradual withdrawal of the bridge 6 liquid occurs along the clot fibre exposing the fibre 7 when the parts are separated. This is represented as step 5. In other words, the cycle from steps 1 to 4 and back to 1 are repeated continuously at a rate of 0.1-10 cycles per second, for example until a fibrin clot 7 is observed and the cycle is diverted from phase 4 to phase 5 rather than to phase 1. It is the detection of the fibre 7 which indicates the termination of the procedure and hence indicates that a clot has been formed.

Referring to FIG. 2, there is shown apparatus for implementing the above described procedure. In FIG. 2 reference numeral 0 represents the first step. A sample of blood 11 is dispensed within a zone defined by a container 8. Located above the container 8 is a probe 9 which has a hydrophilic element 10 positioned at the end of the probe 9. As can be seen in phase 0, the probe does not contact the blood sample 11. The hydrophilic element 10 may be glass, cellulose or any wettable material. In phase 3 the probe 9 has been moved such that the hydrophilic element 10 is immersed in the blood sample 11. Adherent force between the blood and the hydrophilic element 10 causes a bridge 6, as for example shown in FIG. 1, to form between the two system components. This is depicted in FIG. 2 by reference numeral 4. In phase 1 the probe 9 has been moved a sufficient distance away from the container 8 such that the surface tension forces supporting bridge 6 have been overcome and blood sample 11 has become fully separated from a droplet of blood 12 which continues to adhere to the hydrophilic element 10 of the probe 9. The volume surrounding the hydrophilic element 10 comprises a second zone which contains a second part or droplet of blood 12. Sample 11 and droplet 12 comprise the entire blood sample.

The sequence is thereafter repeated as in the system of FIG. 1 from phases 1 to 4 and back to 1 until a fibrin clot is formed and becomes entrained in bridge 6 of phase 4. As the probe 9 moves to the position of phase 1, the fluid comprising bridge 6 is gradually drawn by surface tension into blood sample 11 and droplet 12, leaving the fibrin clot 7 suspended between droplet 12 and blood sample 11 as illustrated in FIG. 2 by phase 5.

Referring to FIG. 3, there is shown a system for dispensing a blood sample useful for detecting the formation of a fibrin clot. In phase 00 blood 15 is drawn from a natural or artificial blood vessel 14 through a hollow needle 17 and into flexible tubing 16. This process is implemented by means of a pump 20 such as for example a peristaltic pump. Thereafter, the blood 15 is transferred through a hollow probe 19 into the zone defined by a container 18 and comprises a blood sample 21. It is noted that blood sample 21 and container 18 corresponds to container 8 and sample 11 of FIG. 2. Upon cessation of the pumping action and the withdrawal of the probe 19 from the zone of container 18, a protruding or exposed surface 22 of blood 15 remains in contact with the probe 19 as depicted in FIG. 3 as phase 1. Thereafter, clot detection may be accomplished by means of the system equivalent to that of FIG. 2 in which the hydrophilic element 10 has been replaced by the hollow volume of the probe 19 in FIG. 3. In both the systems of FIGS. 2 and 3 detection of the fibrin clot 7 may be accomplished by manual or photo-optical observations. However, as a practical matter, it is difficult to implement automated electronic fibrin clot detection by the optical approach because the location and size of the clot are uncertain.

However, if the probe 19 and container 18 comprise electrodes connected to the input terminals 28 of a conductance measurement circuit 30, as shown in FIG. 4A, then the absence of a fibrin clot in FIG. 4A equivalent to a phase 1 condition in FIGS. 2 and 3, will be signified by a zero conductance indication by the circuit 30. Whereas, the presence of a fibrin clot 7 in phase 5 of FIG. 2 or FIG. 4B, for example, will be indicative of an non-zero conductance measurement as demonstrated in FIG. 4B.

The circuitry 30 may comprise an ordinary ohmeter or other circuitry to indicate the lower resistance path generated by the formation of the clot 7. One purpose of fibrin cloth detection systems such as those illustrated in FIGS. 1 to 4 is to function as the sensing element of a clot timing system. Hence a timer is started when blood sample 11 or 21 is in a state ready to begin the analysis, as for example phases 00, 0, or 1 and is stopped when a clot is identified as in phase 5.

Thus as shown in FIG. 4B, the device 30 may be directly connected to a timer 40 which timer is activated via input 41 when the test commences and which timer 40 is automatically turned off when the fibrin clot 7 is detected. Such timing techniques are well known in the art and many examples can be had by referring to the prior art. Additional applications of such systems maybe used in conjunction with the addition of reagents to the blood samples. For example, in FIG. 2 a reagent might be initally adhered or secured to the hydrophilic element 10 in phase 0. Upon reaching phase 3, the reagents are brought into contact with the blood sample 11 and mixed therewith by diffusion and/or convection.

Timing in such a system would also start upon reaching the phase 3 condition. Alternatively, the reagent may be initially deposited in the container 8 or 18 and the blood sample is thereafter dispensed into the container as in phase 00 of FIG. 3. In this case the timing would start as the blood sample 21 first enters container 18 during phase 00.

Referring to FIG. 5, there is illustrated apparatus for detecting the formation of a clot in whole blood or plasma.

FIG. 5A depicts the first phase indicated as phase 000. The apparatus consists of a cylindrical syringe consisting of a main body 42 having an internal hollow including a test volume containing reservoir 38. Located within the hollow of housing 42 is a piston member 23. The piston member 23 has a central aperture or cavity 24 through which is inserted a probe 39 which is analogous to probe 9 and probe 19 of FIGS. 2 and 3. The housing contains a metallic hypodermic needle 37 which needle is inserted into a vessel or blood source 34 which has whole blood or plasma 35 directed therethrough. The end of the rod 39 is associated with a plunger 40 which is electrically conductive. A keeper 49 prevents the plunger 40 from being pushed into the syringe body 42 beyond an initial penetration. The piston 23 is fabricated from an elastomeric material which deforms at the inner walls 31 of the syringe body 42 to form a pneumatic seal. The rod 39 or probe 39 which is associated with the plunger 40 is hydraulically and pneumatically sealed as it passes through the aperture 27 in the center of the piston 23. The cavity 24 which is of a larger diameter than aperture 27 is centrally located along the axis of piston 23 forming a seat 32 at the intersection of aperture 27 and cavity 24.

An expanded section 48 at the end of the plunger 40 within cavity 24 transfers force to the piston 23 through the seat 32 when force is applied on the plunger 40 to withdraw the plunger from the syringe body 42. A hydrophilic material 50 is applied to the end of the expanded section 48 of the probe 39. Granular or liquid reagent 25 is sealed in cavity 24 by a rupturable membrane 28 which may be adhesively applied to the lower end of piston 23 and held in position. In the phase depicted in FIG. 5A, the apparatus is shown as the hypodermic needle 37 has penetrated the wall of the vessel 34 and is immersed in the blood 35. Piston 23 is in its initial lower most position within the syringe body 42. The keeper 49 is positioned between the plunger handle 41 and the upper surface 33 of the syringe body 42 such that the plunger 40 cannot be moved inward relative to piston 23.

In phase 0 depicted in FIG. 5B, the plunger 40 has been pulled outwardly from the syringe body 42 causing the piston 23 to be moved to its upper-most position within the syringe body 42. A vacuum is thereby produced within the test volume reservoir 38 of the syringe which in turn draws blood sample 11 from blood 35 in vessel 34 into the test volume reservoir 38.

Referring to 5C through 5F, it is shown that in phases 3, 4, 1 and 5 the needle 37 has been withdrawn from vessel 34. The keeper 49 has been removed and the apparatus placed in a fixture comprising electrical spring contacts 54 and 55 and a reciprocating impeller 56. The spring contact 54 is in electrical contact with the hypodermic needle 37. In phase 3 as shown in FIG. 5C, the impeller 56 has pushed plunger 40 down causing the expanded section 48 to rupture the membrane 28 releasing the reagent 25 which falls and mixes with the blood sample 11 in the reservoir section 38. As the plunger 40 continues its downward motion, the expanded section 48 become completely immersed in the mixture of blood sample 11 and reagent 25. Piston 23 is held by frictional force in its upper most position in syringe body 42.

In phase 4 depicted in FIG. 5D the impeller 56 has been moved to withdraw the plunger 40 such that the expanded section 48 and the hydrophilic material 50 are drawn beyond the surface of the blood sample reagent mixture 11/25 but remains connected through the fluid bridge 59 to the mixture 11/25 as a result of the surface tension.

Referring to FIG. 5E in phase 1, the plunger 40 has been further withdrawn such that surface tension can no longer support the fluid bridge 59 and a droplet 52 of the blood/reagent mixture adheres to the hydrophilic material 50. Handle 41 of plunger 40 has been brought into electrical contact with spring contact 55. An electrical conductivity measurement between electrical contacts 54 and 55 is now made which will identify a conductive path between droplet 52 and the blood/reagent mixture 11/25 such as a path defined by a fibrin clot 7 as depicted in FIG. 5F as phase 5. If the conductivity measurement is zero or indicative of an extremely large resistance, this indicates the lack of the presence of fibrin clot.

Thus the impeller 56 begins a downward motion restoring the apparatus to the phase 3 condition of FIG. 5C and then processing is continued. However, if a conductivity measure is found to be significantly greater than zero which is indicative of the presence of a fibrin clot 7 between droplet 52 and the blood/reagent 11/25 mixture as illustrated in FIG. 5F, a signal is generated by the electrical measurement apparatus which is indicative of a test end point and the procedure is terminated. Thus from the above, it is seen that by the use of the above noted methods and apparatus, one can initiate a timer at the start of the procedure which time interval is terminated when a conductivity measurement is had indicating the presence of a fibrin clot. The apparatus is relatively rugged and extremely simple to use and therefore can be employed by laboratory technicians as well as untrained personnel.

In regard to the above, it is noted that in conjunction with the test procedure it is important that the operator record the results of the time period as by manually or automatically recording the time of the first dispensing of the blood sample and recording the time that the clot detection signal appears. It is, of course, understood that this recording technique can be implemented by means of automatic printout devices which can be coupled to the apparatus described or can be manually operated to provide written data indicative of the time periods specified as indicative of the time the sample was dispensed and the time the clot was detected.

It will be apparent that there are many modifications and alterations which will be discerned by those skilled in the art all of which are deemed to be incorporated within the breadth and scope of the claims appended hereto.

I claim:

1. A method of detecting the formation of fibrin clots in whole blood or blood plasma comprising the steps of:
   dispensing a sample of blood to be analyzed in a container,
   moving a probe having a hydrophilic tip into said dispensed sample to cause a first part of said sample to adhere to said probe tip with a second part remaining in said container,
   repeatedly moving said first part of said sample into said second part from a given fixed point at a given distance from said second part and out of said second part to repeatedly join and separate said first and second parts, a fluid bridge being formed between said parts by surface tension and during movement of said first part over a portion of said given distance away from said second part, said given distance being selected so that said fluid bridge collapses when said first part is separated from said second part by said given distance unless a fibrin clot is aligned and entrained within said bridge such that said clot connects said first part to said second part at said given distance, applying an electrical potential between said parts when said first and second parts are separated at said given distance, monitoring the electrical current between said first and second parts when said electrical potential is applied, providing a signal when an electrical current is detected between said first and second parts indicative of the presence of an electrically conductive path between said first and second parts, said path comprising at least one fibrin clot simultaneously connected between both said first and second parts and entrained within said bridge when said first and second parts are separated at said given distance.

2. The method according to claim 1 including the further step of:
mixing a reagent with said blood sample prior to the step of repeatedly moving said first part of said sample into and out of said second part.

3. The method according to claim 1 and including the further step of:
determining the time that has elapsed between said signal, which is representative of said fibrin clot, and the addition of said sample into said container.

4. The method according to claim 3 including the further step of:
recording the results of said timing.

5. Apparatus for detecting the formation of fibrin clots in a whole blood or blood plasma sample, comprising:
a container housing having an internal hollow and having a hollow tubular member communicating with said internal hollow at a first end, with said hollow tubular member adapted to be inserted into a source of blood,
movable plunger means coupled to a second end of said container housing and including a probe means having a hydrophilic probe tip positioned within said internal hollow;
a partition means coupled to said movable plunger means and positioned within said hollow to cause a predetermined volume of blood sample to enter said hollow of said container via said tubular member when said plunger means is moved upwardly from said container housing,
means coupled to said plunger means for positioning said probe tip a given distance from said first end of said container to cause said tip to be positioned at a given fixed point from said predetermined volume of blood sample in said hollow and to thereafter repeatedly move said probe tip in and out of said sample to cause a given blood sample to adhere to said tip and to move from said fixed point with said distance selected to allow a surface tension bridge to form between said probe tip end and said sample whereby if a fibrin clot is entrained within said bridge said clot connects said plunger means via said probe tip to said sample and if a clot is not entrained said bridge will collapse when said probe tip is at said fixed point,
detecting means coupled between said plunger means and said tubular member means and responsive to said connection to provide an indication of the presence of said clot when said probe tip is separated from said sample at said given distance.

6. The apparatus according to claim 5 further including a rupturable membrane means containing a blood reagent and located within said internal hollow and positioned to coact with said partition means when moved upwardly to rupture said membrane means to discharge said reagent into said blood sample.

7. In an apparatus for detecting the formation of fibrin clots in a whole blood or blood plasma sample, said apparatus of the class including a movable probe positioned to move in and out of a blood sample contained in a blood reservoir and to provide an indication when a blood clot connects said probe to said reservoir, the improvement in combination therewith, comprising:
a hydrophilic probe tip connected to the end of said movable probe and positioned so that when said probe tip is moved into said reservoir said tip causes a blood sample to adhere thereto, with said tip having said adhered sample restrained to move away from said reservoir at a given selected distance so that a fluid bridge is formed between said adhered sample and said reservoir during probe movement where said bridge will collapse at said given distance unless a fibrin clot is entrained and aligned within said bridge to cause said probe tip to therefore be connected to said reservoir solely by said entrained clot and independent of any clots formed in said reservoir, means for detecting the presence of said entrained fibrin clot which connects said probe tip to said reservoir, and activatable timing means which is activated when said sample adheres to said probe tip for beginning a time period and for terminating said time period when said fibrin clot connects said reservoir to said probe tip.

8. The apparatus according to claim 7 in which said means for detecting the presence of said fibrin clot comprises means for measuring the electrical conductance between said probe tip and said reservoir when separated by said given distance.

9. The apparatus according to claim 7 wherein said means for detecting the presence of said clot includes electrical conductivity measuring means having one input terminal coupled to said probe and a second input terminal connected to said reservoir.

10. An apparatus for detecting the formation of fibrin clots in a whole blood or blood plasma sample, comprising:
a probe having a hydrophilic end to form a surface to which a sample of blood will adhere indicative of a first zone of blood,
means for positioning said probe end a given distance from a sample of blood indicative of a second zone,
means for positioning relative motion between said probe end and said sample to cause said probe end to move in and out of said sample to cause blood to adhere to said probe end indicative of said first zone and to continue said motion to repeatedly join and separate said first and second zones at said given distance to form a fluid bridge from said first and second blood zone samples which bridge is formed by surface tension between said zones and which bridge will collapse at said given distance when a fibrin clot is not entrained and aligned within said bridge, with an entrained fibrin clot serving to connect said zones together at said given distance,
means for measuring the electrical conductance between said zones when said zones are separated by said given distance,
means for generating a signal when an electrical conductance is detected indicative of an electrically conductive path between said zones manifesting the presence of an entrained fibrin clot within said fluid bridge and aligned between said zones to electrically connect said first zone to said second zone, activatable timing means which is activated when said sample first adheres to said probe and which is terminated upon generation of said signal indicative of said electrically conductive path.

* * * * *